United States Patent [19]
Geiste

[11] Patent Number: 5,366,133
[45] Date of Patent: Nov. 22, 1994

[54] SURGICAL FASTENING APPARATUS WITH SHIPPING INTERLOCK

[75] Inventor: Robert J. Geiste, Milford, Conn.

[73] Assignee: United States Surgical Corporation, Norwalk, Conn.

[21] Appl. No.: 982,019

[22] Filed: Nov. 24, 1992

Related U.S. Application Data

[63] Continuation of Ser. No. 779,063, Oct. 18, 1991, abandoned.

[51] Int. Cl.⁵ .................................... A61B 17/072
[52] U.S. Cl. ........................... 227/175; 227/19; 227/8
[58] Field of Search .................. 222/8, 175, 176, 177, 222/178, 19

[56] References Cited

U.S. PATENT DOCUMENTS

| | | |
|---|---|---|
| 2,174,219 | 9/1939 | Balma . |
| 2,246,647 | 6/1941 | Vancura . |
| 3,079,606 | 3/1963 | Bobrov et al. . |
| 3,490,675 | 1/1970 | Green et al. . |
| 3,499,591 | 3/1970 | Green . |
| 3,844,289 | 10/1974 | Noiles . |
| 4,086,926 | 5/1978 | Green et al. . |
| 4,202,480 | 5/1980 | Annett . |
| 4,256,251 | 3/1981 | Moshofsky . |
| 4,351,466 | 9/1982 | Noiles ........................... 227/8 |
| 4,391,401 | 7/1983 | Moshofsky . |
| 4,473,077 | 9/1984 | Noiles et al. . |
| 4,519,532 | 5/1985 | Foslien . |
| 4,520,817 | 6/1985 | Green . |
| 4,576,167 | 3/1986 | Noiles . |
| 4,591,085 | 5/1986 | Di Giovanni . |
| 4,633,861 | 1/1987 | Chow et al. . |
| 4,633,874 | 1/1987 | Chow et al. .................. 227/19 X |
| 4,664,305 | 5/1987 | Blake, III et al. . |
| 4,809,898 | 3/1989 | Gassner et al. . |
| 4,892,244 | 1/1990 | Fox et al. . |
| 4,900,263 | 2/1990 | Manassero et al. . |
| 4,955,959 | 9/1990 | Tompkins et al. . |
| 5,031,814 | 7/1991 | Tompkins et al. . |
| 5,083,695 | 1/1992 | Foslien et al. .................. 227/175 X |

FOREIGN PATENT DOCUMENTS 3735164  11/1988  Germany .

OTHER PUBLICATIONS

United States Surgical Corporation, Norwalk, Conn. copyright 1989.

*Primary Examiner*—Rinaldi I. Rada

[57] ABSTRACT

A surgical fastener applying apparatus is provided with a shipping interlock to prevent premature actuation of the apparatus by the jostling and vibrations which normally occur during shipment of the apparatus from the supplier to the user. The shipping interlock includes a projection extending from the cam bar retainer and initially disposed through an elongated aperture in an interlock plate having an open distal end. The aperture has a narrow neck portion through which the projection can pass only with sufficient force applied to the cam bar retainer. The shipping interlock is adapted to permit passage of the projecting member when the force exceeds the normally expected forces from jostling of cargo to insure that actuation of the apparatus is intentional.

29 Claims, 8 Drawing Sheets

SURGICAL FASTENING APPARATUS WITH SHIPPING INTERLOCK

This is a continuation of copending application Ser. No. 07/779,063 filed on Oct. 18, 1991 now abandoned.

BACKGROUND OF THE INVENTION

1. Field of the Invention

This invention relates to surgical fastening apparatus and specifically to an improved surgical fastening apparatus containing an interlock to prevent movement of the cam bar retainer during shipping or handling of the instrument.

2. Background of the Prior Art

Surgical fastening apparatus for placing gastro intestinal anastomoses are known in the art. Such apparatus are used for suturing gastric and intestinal walls with spaced parallel rows of longitudinally aligned staples or surgical fasteners. For example, Bobroy et al. (U.S. Pat. No. 3,079,606) discloses an instrument for suturing gastric and intestinal walls with metal staples by inserting the tips of the instrument into the lumens of the organs to be sutured through apertures in the walls of the organs. The apparatus comprises a two part frame, each part having finger like projections or forks which are inserted respectively into the apertures in the walls of the organs to be sutured. The frame parts are hinged together with the body tissue held between the forks. When the instrument is actuated, longitudinally moving cam bars contact staple drive members in one of the forks, thereby pushing the surgical staples through the body tissue and into an anvil in the opposite fork. A knife blade between the cam bars creates an incision between the parallel rows of staples. It should be noted, however, that the knife blade is an optional feature. The instrument may be used to fasten body tissue without creating an incision between the rows of staples.

Green et al. (U.S. Pat. No. 3,490,675) discloses an improved instrument of type discussed above, the improved instrument laying down double rows of staples on each side of the incision.

A further improvement in this type of instrument is disclosed in Green (U.S. Pat. No. 3,499,591). The further improved apparatus incorporates an improved structure for the staple-containing cartridge, the pusher assembly which includes the cam bars and knife, and the staple driving members. The contents of the above mentioned patents are incorporated by reference herein in their entirety.

During shipment of the apparatus from the supplier to the user, it may happen that jostling of the cargo during shipment causes the thrust knob and cam bar mechanism to move forward. This can cause premature firing of the staples.

A known shipping interlock is illustrated in FIG. 10, below wherein shipping interlock 190, which comprises a plate member attached to a stationary carrier 134, includes an aperture 191 in the plate. An integral member 146 initially projects from the cam bar retainer 138 through aperture 191. The projection 146 is fabricated from a deformable material such as plastic. To actuate the apparatus, the cam bar retainer 138 is moved distally to advance cam bar 132. This requires the top portion of projection 146 to be sheared off as the cam bar retainer 138 is pushed forward. The force required to shear off the top of projection 146 is easily applied by a surgeon, but higher than forces generally developed during jostling of cargo during shipment.

While the prior known shipping interlock has been useful, we have provided an alternative shipping interlock which functions in a different manner to prevent inadvertent movement of the actuation mechanism of the apparatus as would occur, for example, during shipping and transportation.

SUMMARY

An apparatus for applying surgical fasteners is provided herein. The fasteners can be, for example, metal staples with deformable legs or they can be bioabsorbable fasteners which engage retainers. The fastener applying apparatus comprises: a frame; cartridge means for carrying a plurality of surgical fasteners; means for effecting closure of the fasteners; a stationary carrier receivable into the frame; and a pusher assembly slidably mountable within the stationary carrier. The pusher assembly includes, at least one cam bar for pushing the fasteners from said cartridge into the closure means, a cam bar retainer for mounting the cam bar(s), the cam bar retainer being movable in response to user applied pressure, and optionally a knife member. The apparatus of the present invention further includes a shipping interlock for preventing premature actuation of the surgical fastener. The shipping interlock includes deformable means engagable with the cam bar retainer to prevent premature actuation of the apparatus. Preferably, the shipping interlock comprises a resilient member such as a spring clip with legs defining an aperture for receiving a projection of the cam bar retainer. The legs are resiliently biased to a first position and movable to an expanded second position to permit passage of the projection through the aperture. The aperture is oriented in the direction of movement of the projection and has a first portion through which the projection is initially disposed, a second portion which is at least as wide as the diameter of the projection and which has an opening to permit exit of the projection from the aperture, and a neck portion located between the first portion and the distal portion and having a width less the diameter of the projection. The neck portion is resiliently expandable so as to permit passage of the projection therethrough when urged by sufficient pressure applied to the cam bar retainer.

DETAILED DESCRIPTION OF THE PREFERRED EMBODIMENTS

Figure 1:
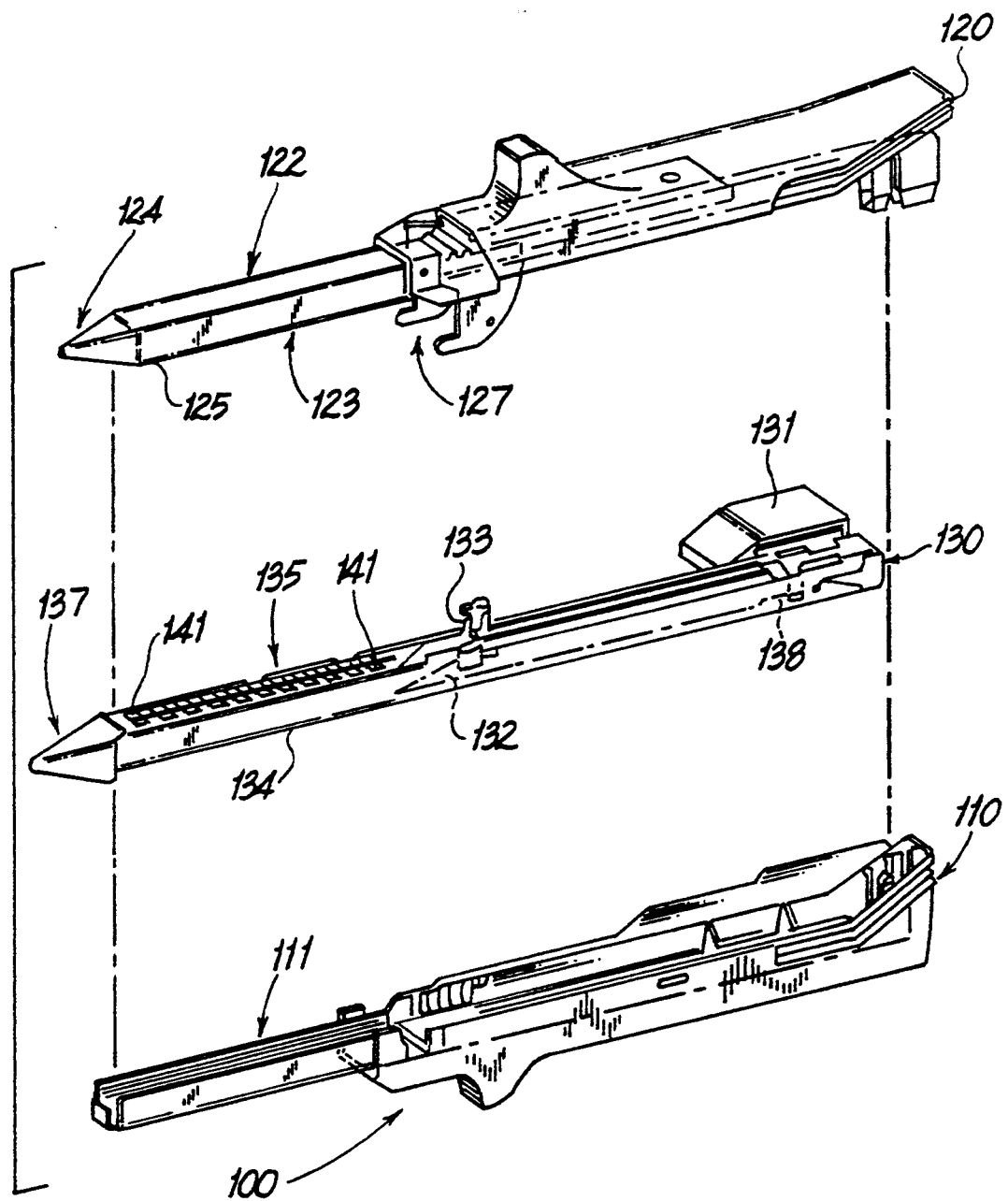
FIG. 1 is an exploded perspective view of the surgical stapling apparatus of the present invention.

Referring to FIG. 1, the surgical stapling apparatus 100 of the present invention comprises a first frame 110 having a distal finger-like projection 111 for holding a cartridge assembly. A second frame 120 has a pair of hinge plates 121 for hingedly connecting to the first frame 110, and a distal finger-like projection 122 for carrying an anvil assembly 123. The anvil assembly 123 is formed of a plate with indentations or depressions 128 as shown more clearly in FIG. 4, for crimping the legs of metal staples. Alternatively, the anvil assembly may include means for holding rows of retainer portions of two-part surgical fasteners to facilitate mutual engagement of the fastener and retainer portions of the two-pan fasteners. Tip 124 allows distal projection 122 to be more easily positioned in body tissue. An optional feature is the resilient deflectable arm 125 which helps to maintain alignment of body tissue positioned between the finger-like projections 111 and 122 and which is preferably attached to tip 124. Deflectable arm 125 may be formed integral with the tip 124, or it may be in the form of a separate attachment.

Figure 2:
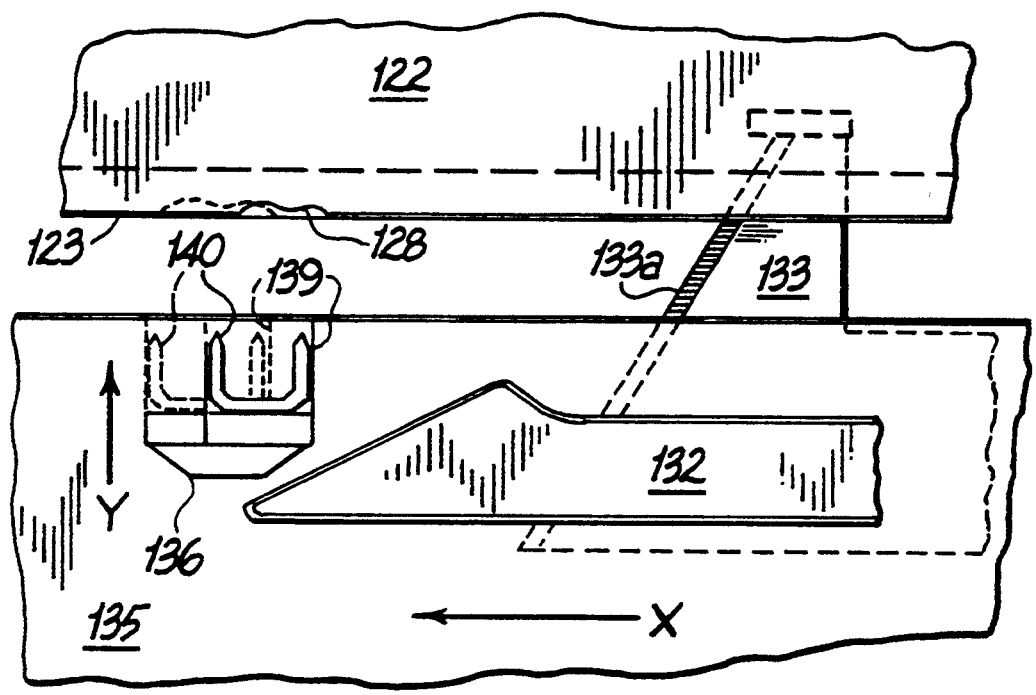
FIG. 2 is an elevational view illustrating the distal end of the apparatus in which fasteners are applied.

Actuating assembly 130 for driving the surgical fasteners is a replaceable insert which includes a pusher assembly having a thrust knob 131, cam bars 132, and optional knife blade 133. The actuating assembly or insert 130 further includes a stationary carrier 134 for holding cartridge assembly 135. Tip 137 at the distal end of the cartridge assembly facilitates positioning body tissue for fastening. Referring also to FIG. 2, cartridge assembly 135 includes pusher members 136 for pushing surgical fasteners out from their respective slots and into contact with the anvil for closure. Cam bars 132 and knife 133 are mounted at their proximal ends to cam bar retainer 138, which is connected to the thrust knob 131 and which provides a means for transferring manually applied force from the thrust knob 131 to the cam bars 132.

In operation the insert 130 is loaded into the first frame 110, and the instrument is then assembled such that the body tissue to be operated upon is located between the cartridge assembly 135 and the anvil assembly 123. The knife 133 is positioned such that it can simultaneously move along slot 126 (see FIG. 4) in the anvil and slot 141 (FIG. 1) in the cartridge assembly. The instrument is then fired by the surgeon's pressing forward (i.e. distally) on the thrust knob 131.

Referring again to FIG. 2, the cam bars 132 and knife 133 are then moved distally and longitudinally along the instrument in the direction indicated by arrow X. The knife 133 creates an incision in the body tissue (not shown) by means of its distal cutting edge 133a, and the cam bars 132 drive the fastener pushers 136 in a direction indicated by arrow Y, which is transverse to that of the longitudinal axis of the instrument. The pusher 136, in turn, drive the fasteners 140 out of their slots 139 and into the depressions 128 in the anvil plate for crimping, thereby fastening the tissue on both sides of the incision. When the operation is completed the used replaceable insert 130 can be disposed, and a new one installed in the apparatus.

Figure 3:
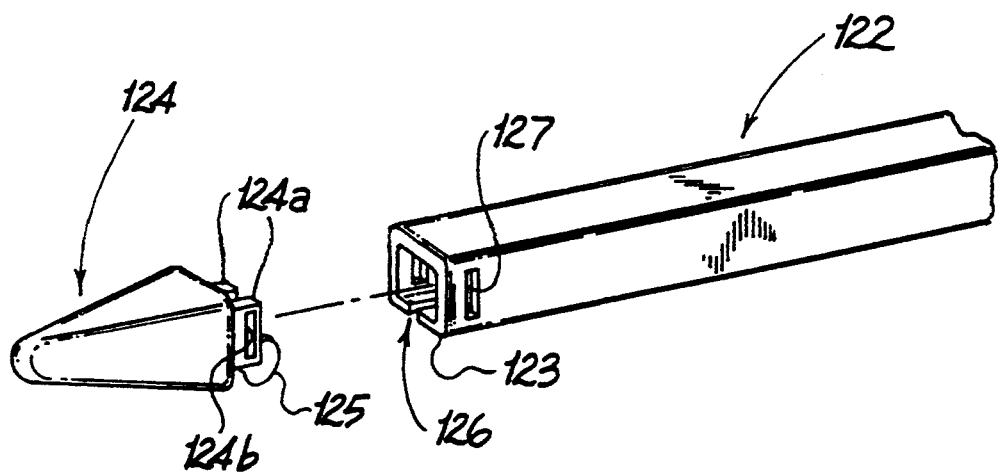
FIG. 3 illustrates the distal end of the anvil.

FIG. 3 illustrates the anvil tip 124 having prongs 124a and detents 124b on the outer sides of the prongs. The detents 124b are for engaging side slots 127 in the distal projection 122. Distal projection 122 carries an anvil assembly which can simply comprise an anvil plate 123 with depressions 128 for crimping the legs of staples. Alternatively, the anvil assembly can house the retainer portions of two-part bioabsorbable surgical fasteners and means for releasably holding them until they are engaged with their respective fastener portions.

Figure 4:
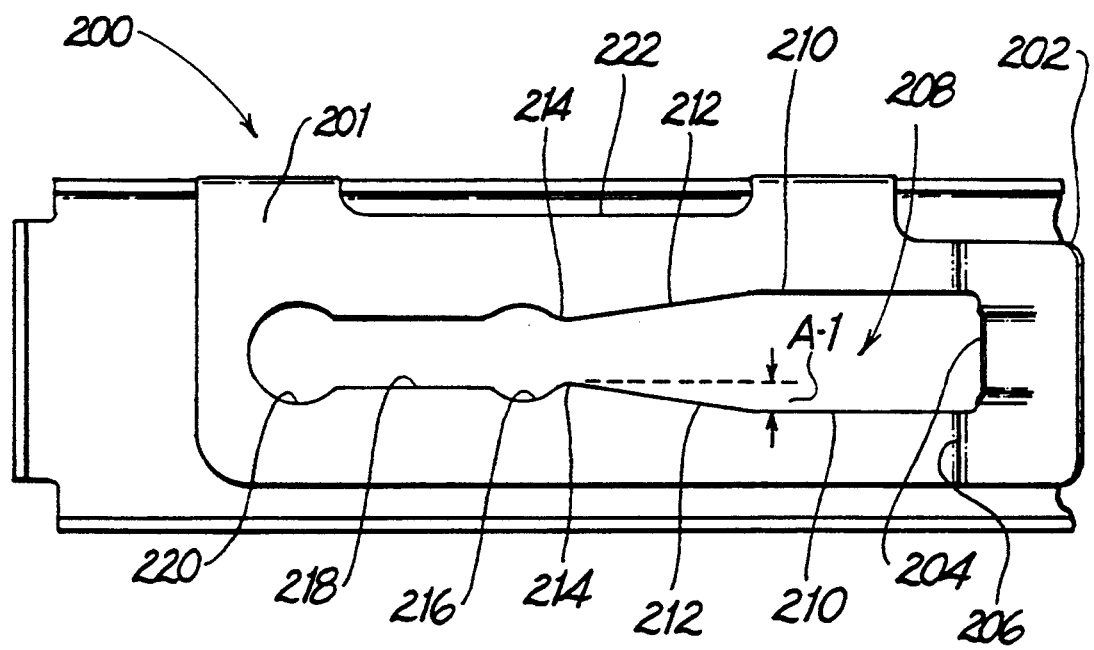
FIGS. 4 and 5 illustrate a plan view and elevational view, respectively, of the shipping interlock of the present invention.
Figure 5:
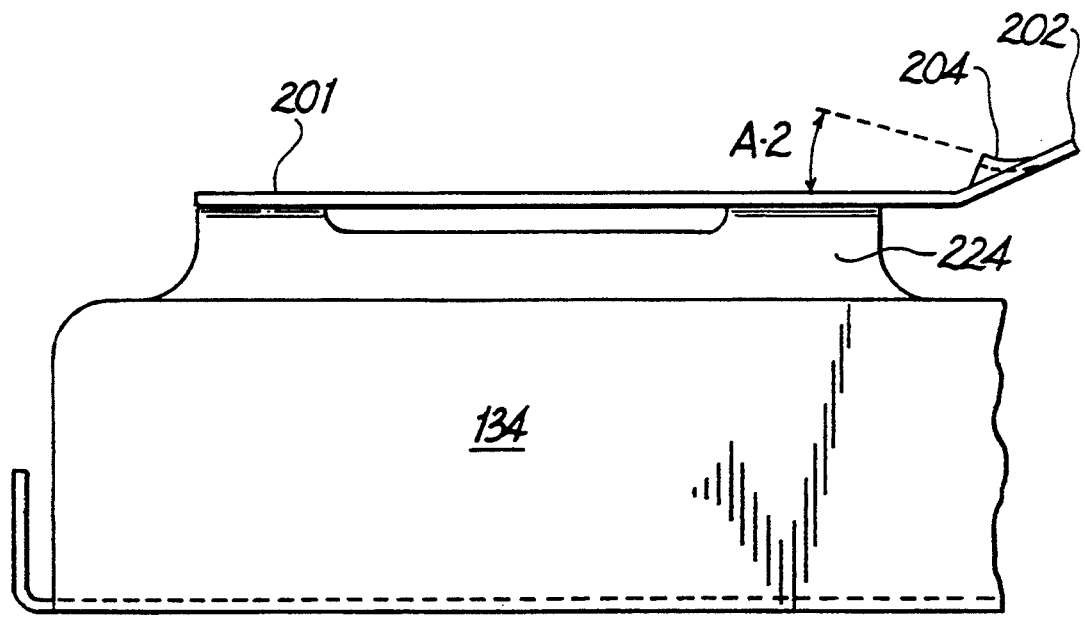

Referring now to FIGS. 4 and 5, the shipping interlock 200 of the present invention comprises a flat plate 201 connected to the stationary carrier 134 by means of a side wall 224. Alternatively, plate 201 and side wall 224 can be integral with the stationary carrier. The flat plate 201 can be fabricated from any material suitable for the function and purpose discussed herein, such as metal (e.g. stainless steel) or plastic. The distal end of the flat plate 201 includes an upraised distally oriented flap portion 202 which angles up from the plate at bend 206 at an angle from the horizontal of from about 10° to about 45° and preferably about 20°. Flap 202 contains a second flap 204 of relatively smaller width and oriented out towards the proximal direction. Flap 204 is angled upward at an angle A-2 from horizontal of from about 10° to 45° and preferably about 20°.

The shipping interlock 200 comprises an elongated central aperture 208 oriented lengthwise with the longitudinal axis of the instrument, which is the direction of movement of the cam bar retainer 138. Aperture 208 has a relatively wide distal portion defined by edges 210 extending substantially parallel with the longitudinal axis of the instrument. Edges 212 define a section with a relatively narrow proximal portion and a relatively wider distal portion. Edges 212 are oriented at an angle A-1 from the longitudinal axis of the instrument wherein A-1 preferably can be from about 5° to about 45°, and more preferably about 10°.

The narrowest portion of the aperture 208, a neck portion, is defined by lips 214. The edges of this neck portion are resilient to allow expansion (deformation) upon passage of the projection 146 as described below. Proximal to lips 214, central aperture 216 is wider than the narrow neck portion but narrower than the distal portion defined by edges 210. The proximal section of aperture 208 is an expansion facilitating portion and includes section 218 defined by rectilinear edges oriented in parallel with the longitudinal axis of the instrument, and a terminal section 220 defined by a curvilinear edge. Notch 222 extends lengthwise along the corner ridge formed by the intersection of side wall 224 and plate 201.

Figure 6:
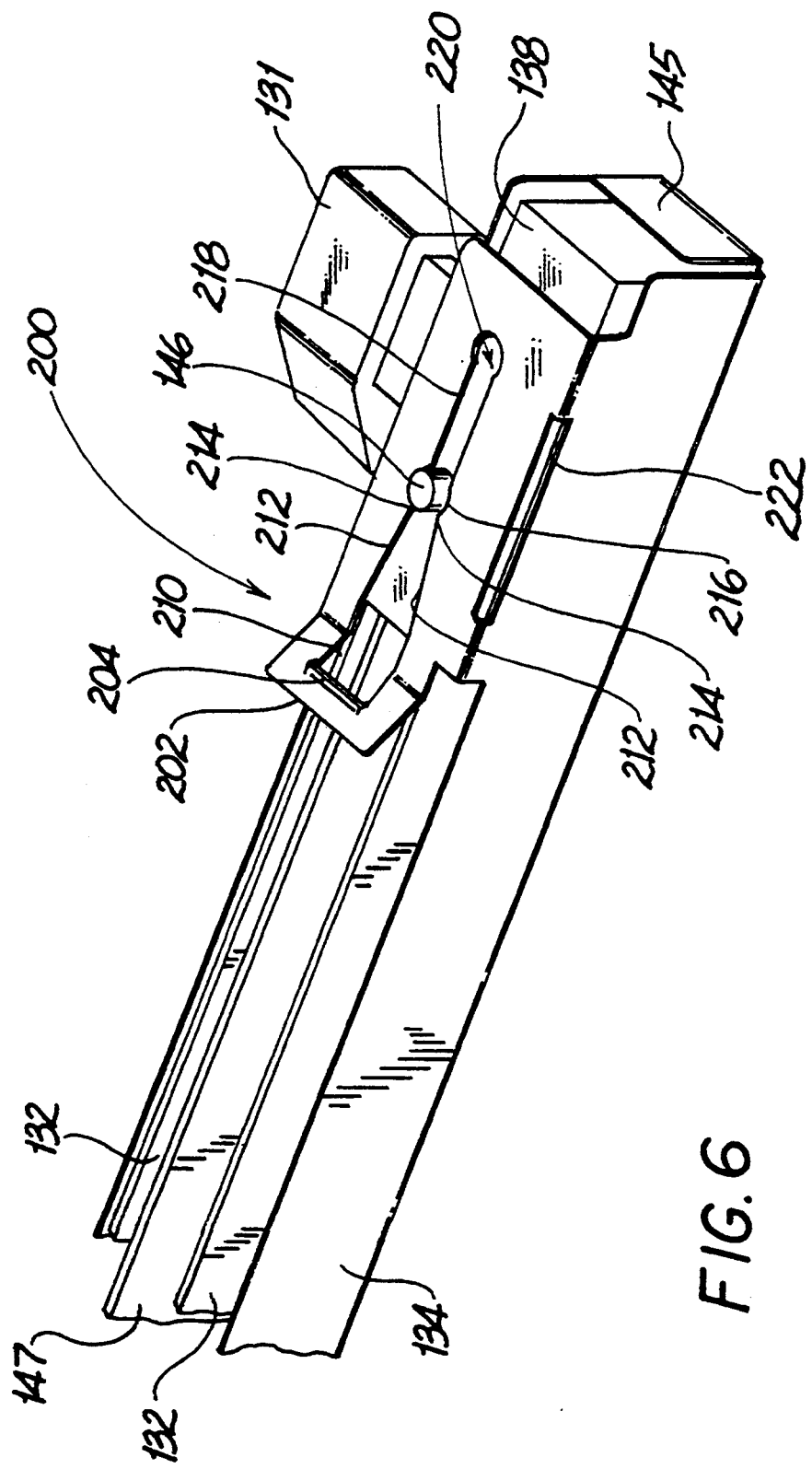
FIGS. 6, 7, and 8 illustrate the operation of the shipping interlock.
Figure 7:
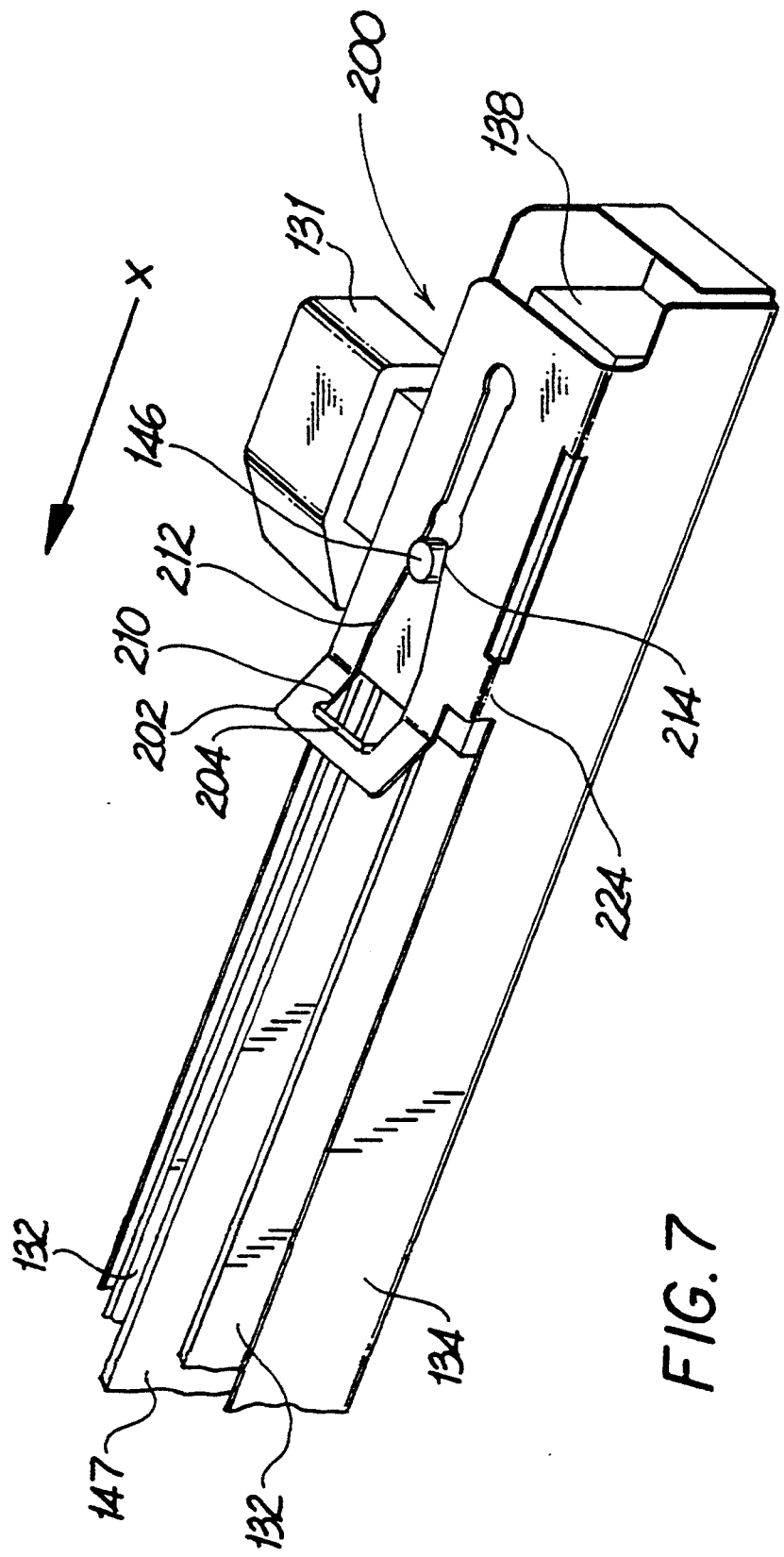
Figure 8:
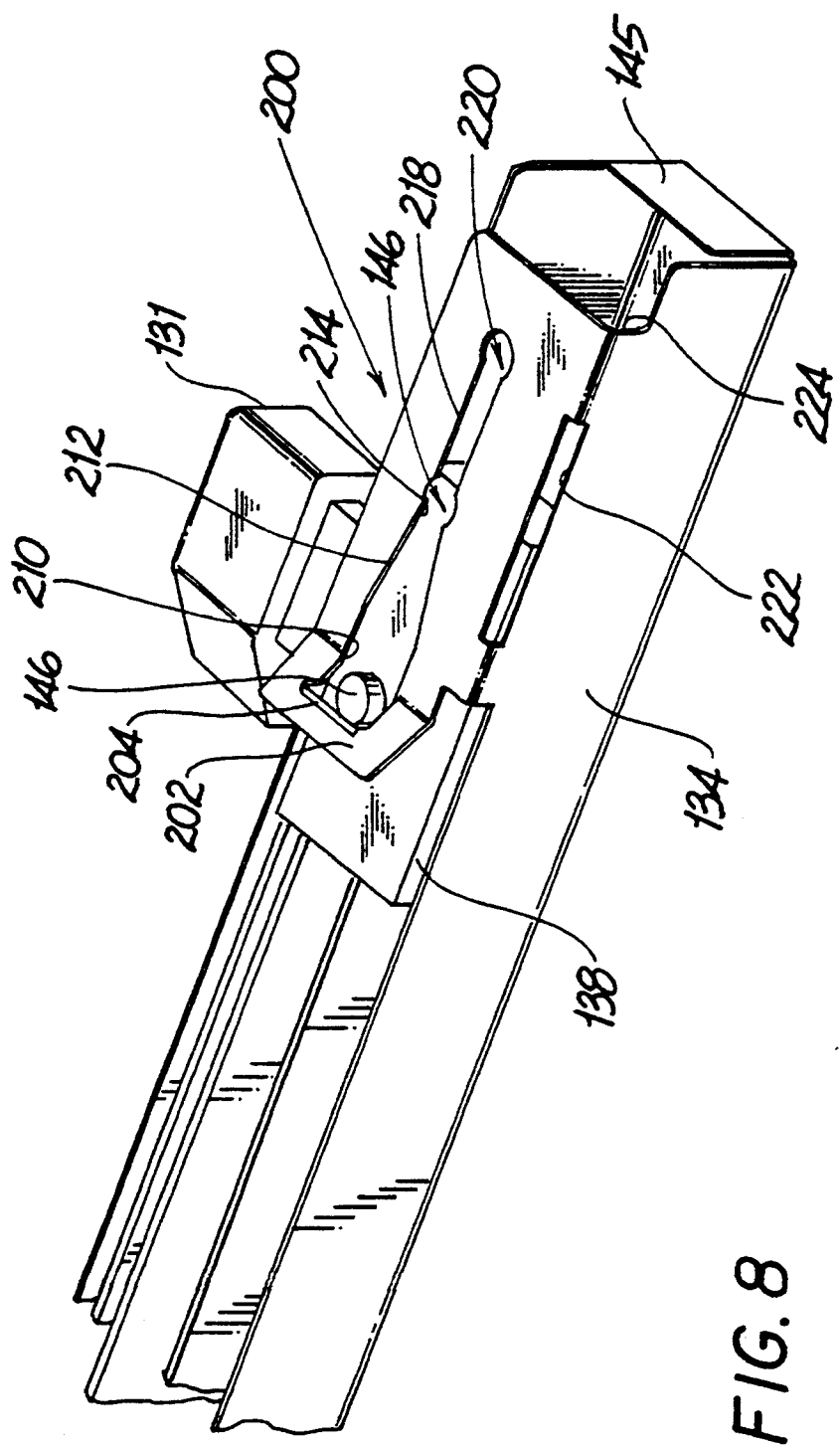

Referring now to FIGS. 6, 7, and 8, the operation of the shipping interlock 200 is illustrated. The initial position of the apparatus is shown in FIG. 6. Cam bar retainer 138 is initially positioned at the proximal end of the stationary carrier 134 and is prevented from proximal movement by proximal flaps 145. Cam bar retainer 138 possesses an upright projection 146 which can be integral with the cam bar retainer 138 or, alternatively, attached to the cam bar retainer 138. In its initial position, projection 146 is disposed through aperture 216 of the shipping interlock 200. The diameter of the projection 146 is about equal to or slightly less than the width of central aperture 216. The diameter of projection 146 is somewhat wider than the width of the elongated central aperture 208 across the lips 214, and across the proximal portion 218. Thus, projection 146 is effectively retained in its initial position by the necessity of applying a strong distally directed force on the thrust knob 131 in order to advance the projection 146 into and distally beyond the lips 214 of the aperture. The shipping interlock is configured and dimensioned so as to release projection 146 upon application to the thrust knob of a force of predetermined magnitude chosen so as to preclude actuation of the instrument during shipping, but to permit actuation by a surgeon. Most forces developed by the ordinary jostling of cargo during shipment will be below such magnitude. However, when in use, the intentional application of pressure on the thrust knob 131 by a surgeon produces force of such direction and magnitude so as to overcome the shipping interlock 200. As shown in FIG. 7, when force is applied to thrust knob 131 in the direction shown by arrow X, the cam bar retainer 138 is advanced to the position as shown in FIG. 7, with the projection 146 passing between lips 214. In order to accommodate the projection 146, the aperture width between lips 214 increases due to the resiliency of interlock 200 to allow passage of the projection therethrough. Providing an extended proximal aperture, portions 218 and 220 facilitate expansion at the lips 214.

When the projection 146 has advanced distally through the narrow portion of aperture 208 between lips 214, it enters the wider portions 212 and 210. FIG. 8 illustrates the configuration of the apparatus as the projection 146 passes through aperture 208 under the inclined flap 202. Inclined flap 202 facilitates the proximal movement of the cam bar retainer 138 by allowing it to slide more easily thereunder when the cam bar retainer 138 is retracted to its original position after firing of the fasteners. The reverse flap 204 facilitates the distal movement of the cam bar retainer 138 by riding over the top of projection 146 as the cam bar retainer passes therethrough.

From this point the thrust bar 131 is advanced until the staples are fired, and it is then retracted to the initial position as shown in FIG. 6.

Alternatively, the shipping interlock of the present invention may be used in conjunction with the instruments disclosed in U.S. Pat. Nos. 4,955,959 and 5,031,814, both of which are herein incorporated by reference.

Figure 9:
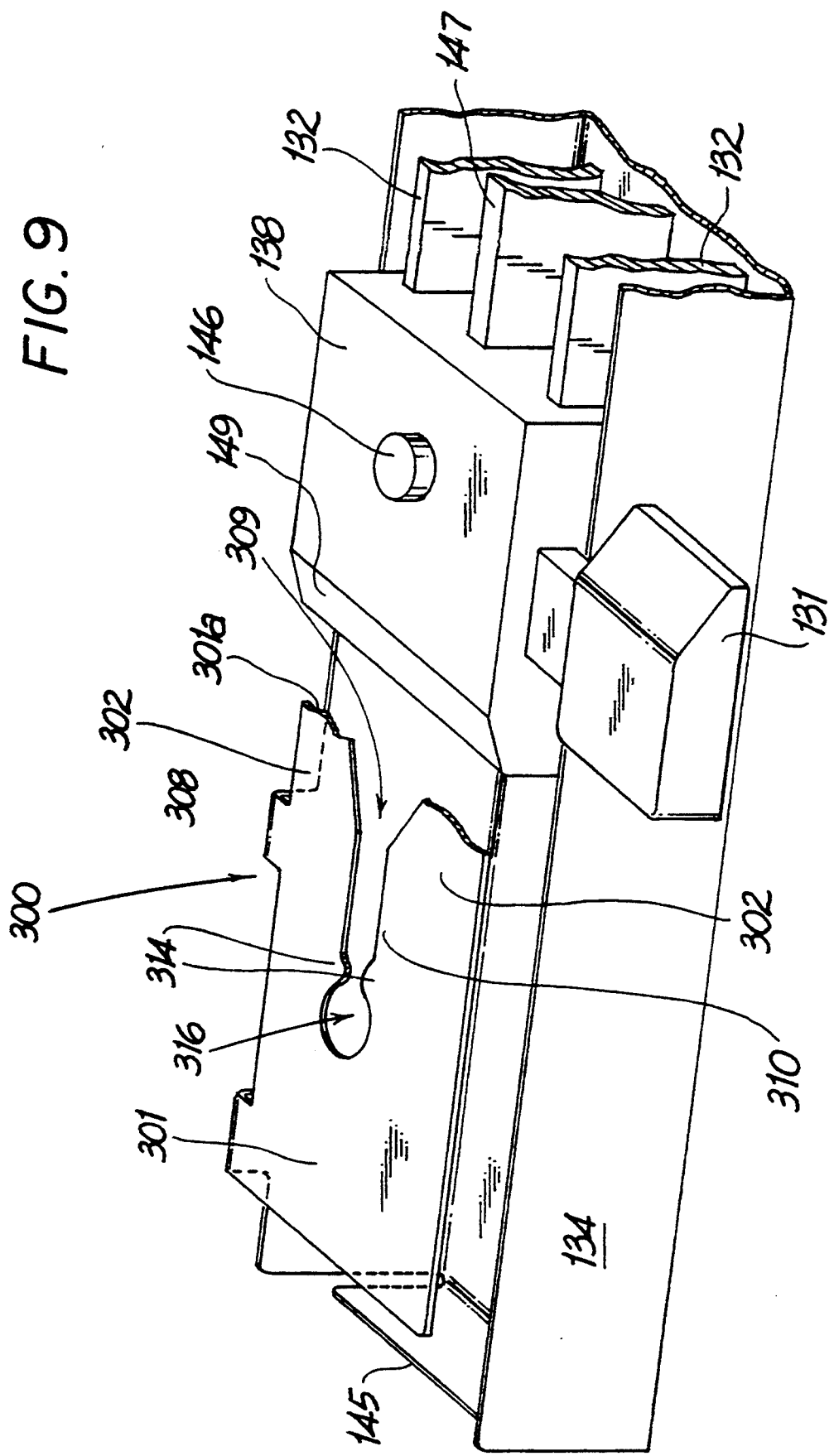
FIG. 9 is a perspective view illustrating an alternative embodiment of the shipping interlock.

FIG. 9 illustrates an alternative embodiment of the present invention wherein shipping interlock 300 includes a flat plate 301 connected to stationary carrier 134. The distal end 301a of plate 301 does not include an inclined flap portion such as flap 202 of embodiment 200. Rather, shipping interlock 300 includes distally pointing legs 302 which define an elongated aperture 308 having an open distal end 309, a relatively wide distal portion, i.e., having a width at least as large as the diameter of projection 146, a longitudinally oriented portion 310 of relatively uniform width, a portion 316 through which the projection 146 is initially disposed, and a narrow neck portion 314 having a width slightly less than the diameter of the projection 146. As with the previously described embodiment 200, a user applied force to the thrust knob 131 is necessary to distally advance the cam bar retainer 138 to move projection 146 out of portion 316 of the aperture and past neck portion 314. With both embodiments the width of neck portion is adapted to permit passage of projection 146 only when the force applied to the thrust bar 131 and cam bar retainer 138 exceeds the normally expected forces occurring with the jostling and vibrations of shipment. An expansion facilitating portion of the aperture, such as 218 or 220 may also be used with shipping interlock 300. A bevelled portion 149 is a preferable feature of cam bar retainer 138 to facilitate retraction of the cam bar retainer to the original position after the staples are fired.

Figure 10:
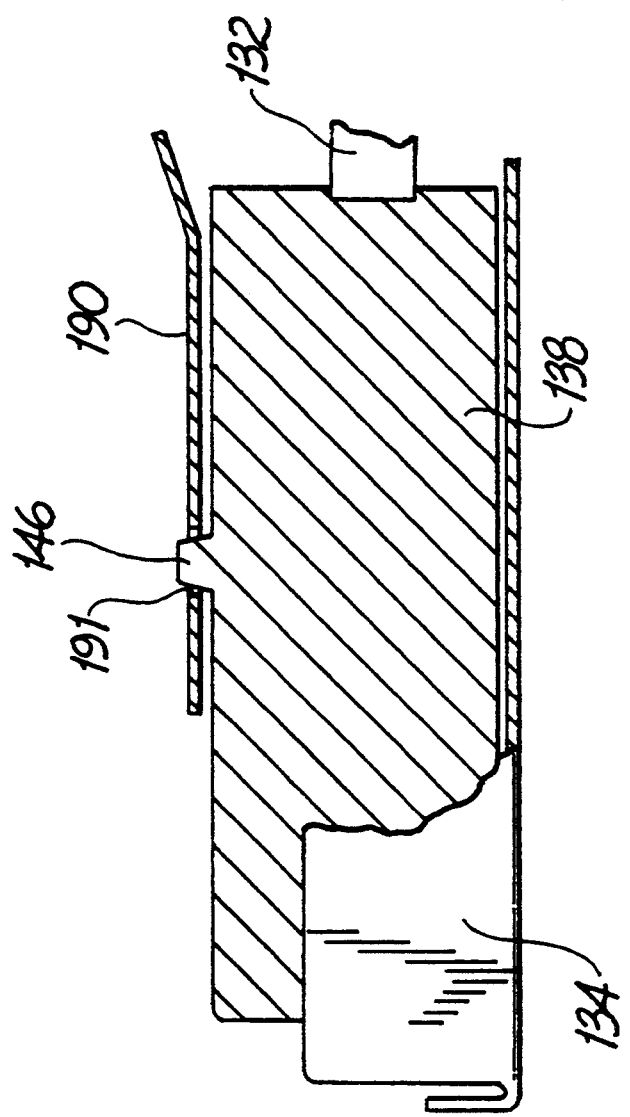
FIG. 10 is a partly sectional view illustrating a prior known shipping interlock.

The shipping interlock of the present invention differs from the prior known interlock 190 as shown in FIG. 10 and discussed earlier. For example, the prior known interlock 190 requires shearing of the projection 146 in order to advance the cam bar retainer 138. Thus, the projection 146 and cam bar retainer 138 were limited to materials of construction with softness and plasticity suitable for permitting shearing to occur, such as polymeric materials. In the present invention, on the other hand, the shipping interlock 200 is deformable and the projection 146 need not be sheared or deformed, thus permitting the use of a wider variety of fabricating materials for the cam bar retainer 138 and projection 146, including materials which would be too rigid or use with the prior art shipping interlock 190.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A surgical fastener applying apparatus, which comprises:
    a) a frame;
    b) a stationary carrier receivable into said frame;
    c) a cartridge for carrying a plurality of surgical fasteners, said cartridge being mountable to said stationary carrier;
    d) closure means mounted to said frame for effecting closure of said fasteners;
    e) a pusher assembly slidably mountable within said stationary carrier, said pusher assembly including at least one cam bar for pushing said fasteners from said cartridge into said closure means, a cam bar retainer for mounting said at least one cam bar, said cam bar retainer being longitudinally movable in response to user applied pressure; and,
    f) a shipping interlock including deformable means engageable with said cam bar retainer for preventing premature actuation of said apparatus, said deformable means being laterally deformed upon actuation of the apparatus to permit disengagement of the cam bar retainer, wherein a projection extends from said cam bar retainer and said deformable means includes an elongated and longitudinally oriented aperture for receiving said projection of said cam bar retainer.

2. The apparatus of claim 1, wherein said aperture comprises:
    a first portion through which said projection is initially disposed,
    a second portion which is at least as wide as a diameter of the projection and which has an opening to permit exit of the projection from the aperture, and
    a neck portion located between said first portion and said second portion and having a width less than the diameter of said projection, said neck portion being resiliently expandable so as to permit passage of the projection therethrough when urged by sufficient pressure applied to said cam bar retainer.

3. The apparatus of claim 2, wherein said apparatus has a longitudinal axis and a distal end and a proximal end, and wherein said second portion of said aperture is disposed distally of said neck portion.

4. The apparatus of claim 4, wherein said apparatus has a longitudinal axis and a distal end and a proximal end, and wherein said aperture of the shipping interlock further includes an expansion facilitating portion located proximally of said first portion, at least part of said expansion facilitating portion having a width less than the diameter of said projection.

5. The apparatus of claim 1, wherein said deformable means and said stationary carrier are integrally constructed.

6. The apparatus of claim 1, further including a plurality of fasteners, wherein said fasteners comprise metal staples with deformable legs.

7. The apparatus of claim 6 wherein the fasteners comprise metal staples with deformable legs, and wherein said closure means comprises an anvil member having a plurality of depressions for crimping the legs of said staples.

8. The apparatus of claim 1, wherein said pusher assembly further comprises a knife member.

9. The apparatus of claim 1, wherein said projection and said cam bar retainer are integrally constructed.

10. The apparatus of claim 1, wherein the shipping interlock comprises a rectangular plate fixed to said stationary carrier.

11. The apparatus of claim 10, wherein said rectangular plate is fabricated from stainless steel.

12. The apparatus of claim 10, wherein said rectangular plate includes an inclined distal portion.

13. In a surgical apparatus possessing an actuating assembly having a cam bar retainer longitudinally movable in response to user applied actuation force for applying a plurality of surgical fasteners to body tissue, an improvement which comprises a shipping interlock for preventing premature actuation of the apparatus prior to its intended use, said shipping interlock including deformable means for releasably holding the cam bar retainer, said deformable means being releasably engageable with the cam bar retainer of the actuating assembly, said deformable means having an elongated longitudinally oriented aperture and being laterally deformed upon movement of the cam bar retainer to release the actuating assembly only in response to applied actuation force which exceeds a predetermined magnitude.

14. The apparatus of claim 13, wherein said deformable means of the shipping interlock is resiliently deformable.

15. The apparatus of claim 14, wherein said deformable means of said shipping interlock is a spring clip having at least two legs defining said aperture between them, said actuating assembly possessing a member receivable into said aperture, said legs being resiliently biased to a first position and movable to an expanded second position to permit passage through said aperture of said member of said actuating assembly.

16. The apparatus of claim 15, wherein said aperture includes a first portion through which said member of said actuating assembly is initially disposed, a neck portion having a width less than a diameter of said member of said actuating assembly, and a distal portion having an opening to permit exit of said member of said actuating assembly from said aperture.

17. The apparatus of claim 16, wherein said deformable means is fixedly attached to a stationary carrier for the actuating assembly.

18. In a surgical apparatus possessing an actuating assembly longitudinally movable in response to user applied actuation force for sequentially applying a plurality of surgical fasteners to body tissue, an improvement which comprises a shipping interlock for preventing premature actuation of the apparatus prior to its intended use, said shipping interlock including planar deformable means for releasably holding a cam bar retainer, said deformable means lying in a first plane and being resiliently deformed in said first plane and in a direction perpendicular to the direction of movement of the surgical fasteners only in response to applied actuation force which exceeds a predetermined magnitude.

19. A surgical fastener applying apparatus, which comprises:
 a) a frame;
 b) cartridge for carrying a plurality of surgical fasteners, said cartridge being mountable to a stationary carrier;
 c) means mounted to said frame for effecting closure of said fasteners;
 d) a stationary carrier receivable into said frame and having a longitudinal axis;
 e) a pusher assembly slidably mountable within said stationary carrier, said pusher assembly including at least one cam bar for pushing said fasteners from said cartridge into said closure means, a cam bar retainer for mounting said at least one cam bar, said cam bar retainer having a projection attached thereto and being movable in response to user applied pressure; and,
 f) a shipping interlock including a deformable member having an elongated aperture extending along the longitudinal axis for engaging said projection of said cam bar retainer.

20. The apparatus of claim 19, wherein said aperture is oriented in the direction of movement of said projection.

21. The apparatus of claim 20, wherein said aperture comprises a first portion through which said projection is initially disposed,
 a second portion which is at least as wide as the diameter of the projection and which has an opening to permit exit of the projection from the aperture, and
 a neck portion located between said first portion and said distal portion and having a width less than the diameter of said projection, said neck portion being resiliently expandable so as to permit passage of the projection therethrough when urged by sufficient pressure applied to said cam bar retainer.

22. The apparatus of claim 21, wherein said apparatus has a longitudinal axis and a distal end and proximal end, and wherein said second portion of said aperture is disposed distally of said neck portion.

23. The apparatus of claim 21, wherein said aperture of the shipping interlock further includes an expansion facilitating portion located proximally to said first portion, at least part of said expansion facilitating portion located proximally to said first portion, at least part of said expansion facilitating portion having a width less than the diameter of said projection.

24. The apparatus of claim 19, wherein said deformable member and said stationary carrier are integrally constructed.

25. In a surgical apparatus possessing an actuating assembly having a cam bar retainer longitudinally movable in response to user applied actuation force for sequentially applying a plurality of surgical fasteners to body tissue, an improvement which comprises a shipping interlock for preventing premature actuation of the apparatus prior to its intended use, said shipping interlock including deformable means mounted for engagement with the cam bar retainer of the actuating assembly for preventing movement of said cam bar retainer, said deformable means deforming upon actuation of the apparatus and having a first aperture portion for retaining said cam bar retainer in a locked position and a second aperture portion for releasing said cam bar retainer, said cam bar retainer sliding from said first portion to said second portion only in response to applied actuation force which exceeds a predetermined magnitude.

26. In a surgical apparatus possessing a cartridge containing a plurality of surgical fasteners, a frame for mounting the cartridge, and an actuating assembly having a longitudinal axis and at least one cam bar mounted for longitudinal movement in response to user applied actuation force for applying a plurality of surgical fasteners to body tissue, an improvement which comprises a shipping interlock for preventing premature actuation of the apparatus prior to its intended use, said shipping interlock including a spring clip having at least two legs defining an elongated aperture between them, said aperture extending along the longitudinal axis, said actuating assembly possessing a member extending into said aperture, said legs being resiliently biased to a first position and moved to an expanded second position by said member to permit passage through said aperture of said member of said actuating assembly.

27. The apparatus of claim 26, wherein said aperture includes a first portion through which said member of said actuating assembly is initially disposed, a neck portion having a width less than a diameter of said member of said actuating assembly, and a distal portion having an opening to permit exit of said member of said actuating assembly from said aperture.

28. The apparatus of claim 27, wherein said spring clip is fixedly attached to a stationary carrier for the actuating assembly.

29. A surgical fastener applying apparatus, which comprises:
   a) a frame;
   b) cartridge for carrying a plurality of surgical fasteners, said cartridge being mountable to a stationary carrier;
   c) means mounted to said frame for effecting closure of said fasteners;
   d) a stationary carrier receivable into said frame;
   e) a pusher assembly slidably mountable within said stationary carrier, said pusher assembly including at least one cam bar movable from a proximal position to a distal position for pushing said fasteners from said cartridge into said closure means, a cam bar retainer for mounting said at least one cam bar, said cam bar retainer having a projection attached thereto and being movable in response to user applied pressure; and,
   f) a shipping interlock including a deformable member deforming upon movement of said cam bar retainer and having an aperture for engaging said projection of said cam bar retainer, said projection being retained by said deformable member and moving from an initial locked position to a second position released from said deformable member upon distal movement of said cam bar retainer, said projection returning to its locked position upon return of said cam bar retainer to said proximal position.

* * * * *